United States Patent
Lee et al.

(10) Patent No.: US 9,629,607 B2
(45) Date of Patent: Apr. 25, 2017

(54) PACKAGING AND FLUID FILLING OF ULTRASOUND IMAGING CATHETERS

(75) Inventors: Warren Lee, Niskayuna, NY (US); Douglas Glenn Wildes, Ballston Lake, NY (US); Weston Blaine Griffin, Niskayuna, NY (US)

(73) Assignee: GENERAL ELECTRIC COMPANY, Niskayuna, NY (US)

( * ) Notice: Subject to any disclaimer, the term of this patent is extended or adjusted under 35 U.S.C. 154(b) by 2160 days.

(21) Appl. No.: 12/104,247

(22) Filed: Apr. 16, 2008

(65) Prior Publication Data
US 2008/0287798 A1 Nov. 20, 2008

Related U.S. Application Data

(60) Provisional application No. 60/917,993, filed on May 15, 2007.

(51) Int. Cl.
*A61B 8/00* (2006.01)
*A61B 8/12* (2006.01)

(52) U.S. Cl.
CPC ............. *A61B 8/4461* (2013.01); *A61B 8/12* (2013.01); *A61B 8/4281* (2013.01); *A61B 8/445* (2013.01); *Y10T 29/49826* (2015.01)

(58) Field of Classification Search
USPC ........................................................ 204/571
See application file for complete search history.

(56) References Cited

U.S. PATENT DOCUMENTS

| | | | |
|---|---|---|---|
| 4,410,826 A | 10/1983 | Waxman et al. | |
| 4,429,577 A | 2/1984 | Sorenson et al. | |
| 4,951,677 A * | 8/1990 | Crowley et al. | 600/463 |
| 5,002,059 A * | 3/1991 | Crowley et al. | 600/466 |
| 5,133,454 A * | 7/1992 | Hammer | 206/364 |
| 5,178,267 A * | 1/1993 | Grabenkort et al. | 206/210 |
| 5,315,985 A * | 5/1994 | Decarie et al. | 600/101 |
| 5,375,602 A * | 12/1994 | Lancee et al. | 600/463 |
| 5,421,338 A * | 6/1995 | Crowley et al. | 600/463 |
| 5,715,825 A * | 2/1998 | Crowley | 600/462 |
| 5,848,691 A * | 12/1998 | Morris et al. | 206/364 |
| 6,004,269 A * | 12/1999 | Crowley et al. | 600/439 |
| 6,165,127 A * | 12/2000 | Crowley | 600/463 |
| 6,572,553 B2 * | 6/2003 | Crowley | 600/463 |
| 6,602,242 B1 | 8/2003 | Fung et al. | |
| 7,037,271 B2 * | 5/2006 | Crowley | 600/463 |
| 7,235,070 B2 | 6/2007 | Vanney | |
| 7,434,686 B2 * | 10/2008 | Prindle | 206/364 |
| 7,491,176 B2 * | 2/2009 | Mann | 600/564 |
| 7,743,918 B2 * | 6/2010 | Itou et al. | 206/364 |
| 8,303,599 B2 * | 11/2012 | Hess et al. | 606/92 |
| 2002/0099289 A1 * | 7/2002 | Crowley | 600/439 |
| 2002/0188201 A1 * | 12/2002 | Crowley | 600/439 |

(Continued)

*Primary Examiner* — Long V Le
*Assistant Examiner* — Angela M Hoffa
(74) *Attorney, Agent, or Firm* — Fletcher Yoder, P.C.

(57) ABSTRACT

An imaging catheter assembly is presented. The imaging catheter assembly includes an imaging catheter which includes an imaging catheter tip. Further, the imaging catheter assembly includes a fluid reservoir connected to the imaging catheter and configured to deliver fluid through a proximal end of the imaging catheter tip. The imaging catheter assembly also includes a release mechanism configured to cause delivery of the fluid to the imaging catheter tip when activated.

14 Claims, 7 Drawing Sheets

(56) References Cited

U.S. PATENT DOCUMENTS

| | | |
|---|---|---|
| 2005/0015011 A1 | 1/2005 | Liard et al. |
| 2006/0235303 A1 | 10/2006 | Vaezy et al. |
| 2006/0264741 A1* | 11/2006 | Prince .......................... 600/420 |
| 2007/0167813 A1 | 7/2007 | Lee et al. |
| 2007/0167821 A1 | 7/2007 | Lee et al. |
| 2007/0167824 A1 | 7/2007 | Lee et al. |
| 2007/0167825 A1 | 7/2007 | Lee et al. |
| 2007/0167826 A1 | 7/2007 | Lee et al. |
| 2007/0185495 A1* | 8/2007 | Hess et al. ...................... 606/93 |
| 2007/0232923 A1 | 10/2007 | Asuri |

\* cited by examiner

PACKAGING AND FLUID FILLING OF ULTRASOUND IMAGING CATHETERS

CROSS REFERENCE TO RELATED APPLICATIONS

This application claims priority to U.S. Provisional Patent Application No. 60/917,993, entitled "METHODS FOR PACKAGING AND FLUID FILLING OF MECHANICALLY SCANNING ULTRASOUND IMAGING CATHETERS," filed May 15, 2007, which is herein incorporated by reference in its entirety for all purposes.

BACKGROUND

The present disclosure relates generally to ultrasound imaging catheters and, more particularly, to methods for packaging mechanically scanning ultrasound imaging catheters and for filling these imaging catheters with acoustic coupling fluid at or near the time of use.

Acoustic transducers have found application in medical imaging where an acoustic probe is held against a patient and the probe transmits and receives ultrasound waves. The received energy may, in turn, facilitate the imaging of the tissues of the patient. For example, transducers may be employed to image the heart of the patient.

Catheter-based ultrasonic imaging techniques are interventional procedures that generally involve inserting a probe, such as an imaging catheter, into a vein, such as the femoral vein, or an artery. As will be appreciated, catheter-based ultrasonic imaging techniques may be employed for imaging the heart, such as when monitoring and/or directing treatment of atrial fibrillation. Consequently, it is highly desirable that transducer assemblies used in catheters be capable of two-dimensional and/or real-time three-dimensional imaging. Such applications are quite demanding, requiring very small transducer packages that can nevertheless collect large amounts of information.

In some circumstances, it may be desirable to provide some form of acoustic coupling between the transducer assembly and the surrounding housing. Depending on the form the acoustic coupling takes, it may be desirable to test the probe prior to shipping. Such testing, however, should be cleanable such that no residue remains in the shipped product. Further, to the extent that the coupling mechanism is not present in the probe at the time of shipping, it should be easy for the end user to provide the desired acoustic coupling.

BRIEF DESCRIPTION

Briefly, in accordance with aspects of the present technique, an imaging catheter assembly is presented. The imaging catheter assembly includes an imaging catheter which includes an imaging catheter tip. Further, the imaging catheter assembly includes a fluid reservoir connected to the imaging catheter and configured to deliver fluid through a proximal end of the imaging catheter tip. The imaging catheter assembly also includes a release mechanism configured to cause delivery of the fluid to the imaging catheter tip when activated.

In accordance with further aspects of the present technique, a packaging assembly is presented. The packaging assembly includes an imaging catheter which includes an imaging catheter tip and a fill mechanism. The packaging assembly also includes a package configured to hold the imaging catheter tip in a fill orientation to facilitate filling the imaging catheter tip with acoustic coupling fluid upon activation of the fill mechanism.

In accordance with further aspects of the present technique, a method of imaging is presented. The method of imaging includes causing a biasing member to displace acoustic coupling fluid from a fluid reservoir into an imaging catheter tip. The method of imaging also includes inserting the imaging catheter tip into a patient. In addition, the method of imaging includes collecting ultrasound imaging data using a transducer assembly disposed in a distal portion of the imaging catheter tip.

In accordance with yet another aspect of the present technique, a method of manufacturing and testing an imaging catheter is presented. The method includes assembling an imaging catheter. The imaging catheter includes an imaging catheter tip which includes a motor assembly and a transducer assembly. The method also includes testing rotation of the motor and transducer assemblies. In addition, the method includes injecting testing fluid into the imagining catheter tip. Further, the method includes testing acoustic and imaging performance of the imaging catheter tip. Also, the method includes removing the testing fluid from the imaging catheter tip. The method further includes drying and sterilizing the imaging catheter.

In accordance with further aspects of the present technique, an imaging catheter assembly is presented. The imaging catheter assembly includes an imaging catheter which includes an imaging catheter tip. The imaging catheter tip is configured to be automatically filled from a fluid reservoir when a release mechanism is activated.

In accordance with yet further aspects of the present technique, a fill mechanism is presented. The fill mechanism includes a fluid reservoir configured to connect to an imaging catheter tip and to deliver fluid to the imaging catheter tip. The fill mechanism also includes a release mechanism configured to cause delivery of the fluid to the imaging catheter tip when activated.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Imaging probes containing transducer assemblies for obtaining real-time, three-dimensional ultrasound imaging may use a motor assembly to oscillate transducer assemblies about an axis of the imaging probe. In doing so, the transducer assemblies may be capable of obtaining real-time, three-dimensional ultrasound images by sweeping a two-dimensional slice through a three-dimensional volume. Acoustic coupling fluid may be used in conjunction with the transducer assemblies to provide an effective or suitable acoustic transition between the transducer and the surrounding housing. Such imaging probes are typically filled with acoustic coupling fluid at the time of manufacture. Such imaging probes also typically include a fluid barrier to separate the motor from the fluid-filled space that houses the transducer. The barrier is penetrated by a driveshaft that couples the motor to the moving transducer. A fluid seal on the driveshaft prevents or minimizes the leakage of fluid from the transducer space to the motor space.

When the imaging probe is a catheter tip or other very small device intended for imaging in space-constrained regions, the space constraints may preclude isolating the motor from the fluid-filled transducer space. In such scenarios, the presence of the acoustic coupling fluid in the imaging catheter tip for long periods of time before use may prove problematic. For instance, the fluid may gradually seep into the motor and associated gearbox, increasing the risk of performance degradation. For similar reasons, the risk of shelf-life failures may be increased. Also, corrosion and leaching may occur since the fluid is encased in the imaging catheter tip for such a long period of time. Furthermore, sterilization may be more difficult when filling the imaging catheter tip at the time of manufacture. These problems may all result in reduced performance of the imaging catheter. In addition, many typical methods for filling the imaging catheter tip have a tendency to generate bubbles which can cause problems during image data collection.

With the foregoing in mind, using the present technique, the aforementioned limitations may be overcome by filling the imaging catheter with acoustic coupling fluid at or near the time of use of the imaging catheter. For a fill-at-time-of-use scenario, at least two distinct solutions may be possible. A first method may be to fill the imaging catheter with acoustic coupling fluid from the distal end of the imaging catheter. For instance, a syringe may be inserted into a self-sealing port at the distal end of the imaging catheter. While this method may be possible, it may prove difficult to ensure subsequent sealing of the distal filling port. This method may also require the use of an isolation transformer or some other mechanism at the proximal end of the imaging catheter to achieve electrical isolation and patient safety. In addition, a self-sealing distal port may also increase the stiff length of the distal tip. Doing so may reduce the maneuverability of the catheter in the body.

Therefore, a second method of filling the imaging catheter from the proximal end may prove more beneficial. Using such a method, tubing may be employed to direct the fluid internally to the imaging catheter tip. This method may prove to be desirable for introducing acoustic coupling fluid into the imaging catheter tip while maintaining maximum performance. In addition, using this method, it may be possible to fill the imaging catheter tip with acoustic coupling fluid at a controlled rate in order to minimize the likelihood of forcing fluid into the motor and associated gearbox. This controlled rate may also reduce the risk of bubbles becoming trapped within the imaging catheter tip. Pointing the imaging catheter tip downward may also minimize trapped bubbles. Suitable imaging catheter tips for use with acoustic coupling fluid are described herein and also in the US Patent Application entitled "FLUID-FILLABLE ULTRASOUND IMAGING CATHETER TIPS," filed Apr. 16, 2008 by Warren Lee et al., which is herein incorporated by reference in its entirety for all purposes.

The system and methods presented allow for filling of an imaging catheter tip with acoustic coupling fluid at the time of use, such as during or within a short time prior to an examination or imaging session or appointment. In one embodiment, a spring-loaded syringe may be used to introduce the acoustic coupling fluid through a fill tube just prior to use. In such an embodiment, the fill tube may extend through a portion of the imaging catheter body to reach the imaging catheter tip. Air may also be vented via a vent tube. In embodiments where a pre-biased mechanism (such as a spring-loaded syringe) is used, the fluid filling process may be performed accurately and in a repeatable fashion independent of the operator. In addition, the fluid filling process using a pre-biased mechanism may prove easy for a clinician to perform and, therefore, improve user acceptance.

Figure 1:
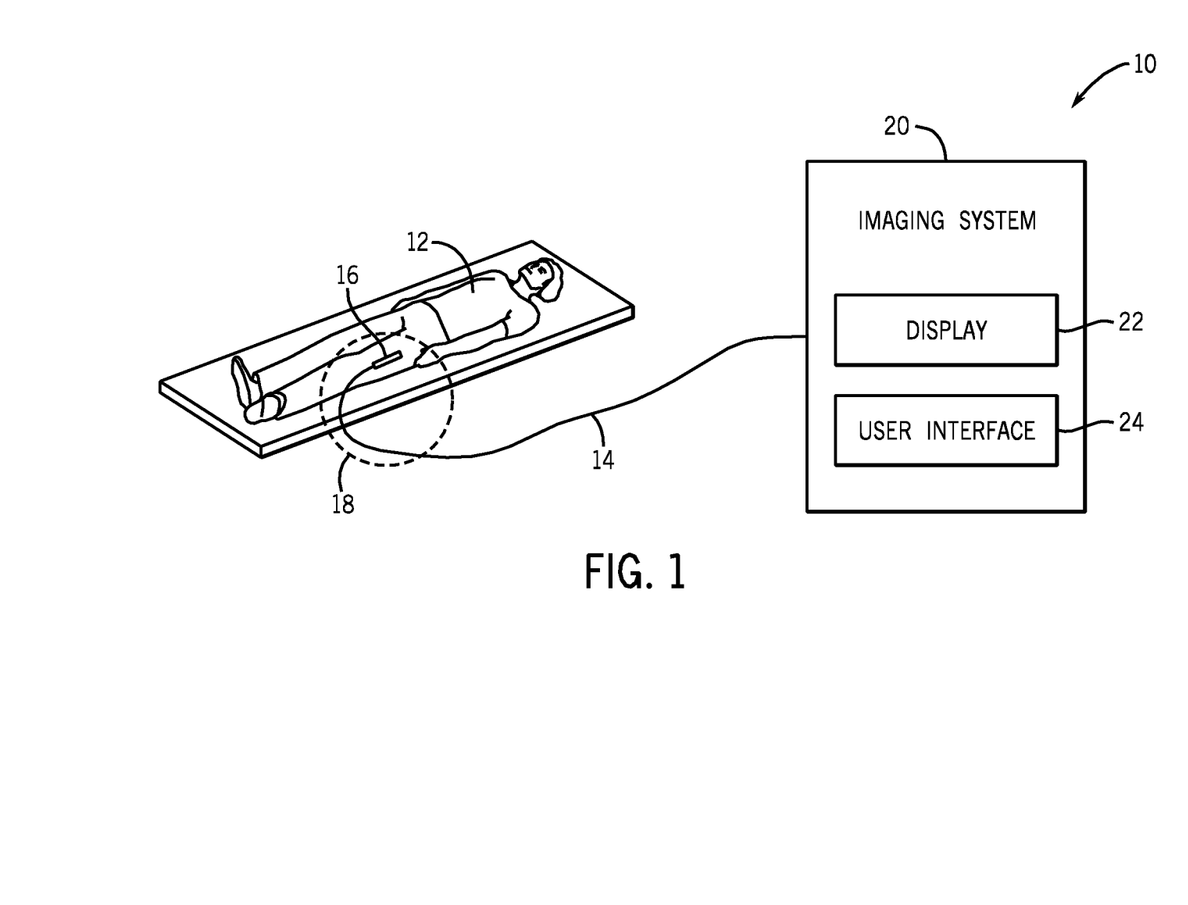
FIG. 1 is a block diagram of an exemplary ultrasound imaging system, in accordance with aspects of the present technique.

With the foregoing general discussion in mind, specific implementations of the present technique are discussed below. FIG. 1 is a block diagram of an exemplary system 10 for use in ultrasound imaging, in accordance with aspects of the present technique. As will be appreciated by those skilled in the art, the figures are for illustrative purposes and are not necessarily drawn to scale. The system 10 may be configured to facilitate acquisition of ultrasound image data from a patient 12 via an imaging catheter 14. For example, the imaging catheter 14 may be configured to acquire ultrasound image data representative of a region of interest in the patient 12 such as the cardiac or pulmonary region. In accordance with aspects of the present technique, the imaging catheter 14 may be configured to function as an invasive probe. It should also be noted that, although the embodiments illustrated are described in the context of a catheter-based probe, other types of invasive probes such as endoscopes, laparoscopes, surgical probes, transrectal probes, transvaginal probes, intracavity probes, probes adapted for interventional procedures, or combinations thereof are also contemplated in conjunction with the present technique. Reference numeral 16 is representative of a portion of the imaging catheter 14 disposed inside the patient 12, such as inserted into a vein. Reference numeral 18 is indicative of a portion of the imaging catheter 14 depicted in greater detail in FIG. 2.

The system 10 may also include an ultrasound imaging system 20 that is in operative association with the imaging catheter 14 and configured to facilitate acquisition of ultrasound image data. It should be noted that although the exemplary embodiments illustrated hereinafter are described in the context of a medical imaging system, such as an ultrasound imaging system, other imaging systems and applications are also contemplated (e.g., industrial applications, such as non-destructive testing, borescopes, and other applications where ultrasound imaging within confined spaces may be used). Additionally, the exemplary embodiments illustrated and described hereinafter may find application in multi-modality imaging systems that employ ultrasound imaging in conjunction with other imaging modalities, position-tracking systems, or other sensor systems.

Further, the ultrasound imaging system 20 may be configured to display an image representative of a current position of the imaging catheter tip within the patient 12. As illustrated in FIG. 1, the ultrasound imaging system 20 may include a display area 22 and a user interface area 24. In accordance with aspects of the present technique, the display area 22 of the ultrasound imaging system 20 may be configured to display a two- or three-dimensional image generated by the ultrasound imaging system 20 based on the image data acquired via the imaging catheter 14. For example, the display area 22 may be a suitable CRT or LCD display on which ultrasound images may be viewed. The user interface area 24 may include an operator interface device configured to aid the operator in identifying a region of interest to be imaged. The operator interface may include a keyboard, mouse, trackball, joystick, touch screen, or any other suitable interface device.

Figure 2:
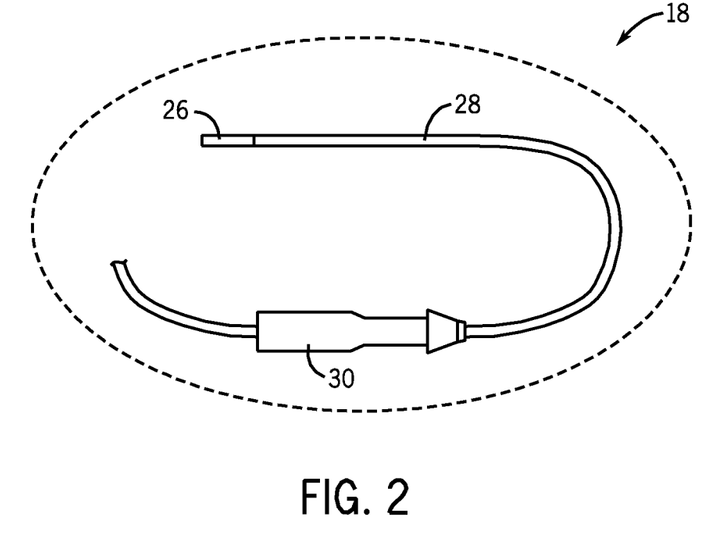
FIG. 2 is a side view of a portion of an invasive probe including an exemplary imaging catheter tip and transducer assembly for use in the system illustrated in FIG. 1, in accordance with aspects of the present technique.

FIG. 2 illustrates an enlarged view of the portion 18 (see FIG. 1) of the imaging catheter 14 (see FIG. 1). As depicted in FIG. 2, the imaging catheter 14 may include a tip 26 on the distal end of a flexible shaft 28. It is this distal tip 26 that houses the transducer assembly and motor assembly as discussed herein. The imaging catheter 14 may also include a handle 30 configured to facilitate an operator manipulating the flexible shaft 28. In the context of this disclosure, points within the imaging catheter 14 which are closer to the handle 30 may be referred to as proximal whereas points within the imaging catheter which are further from the handle 30 may be referred to as distal. The distance between the transducer assembly and the handle 30 may be in a range from about 10 cm to about 150 cm depending on the type of probe and application.

Figure 3:
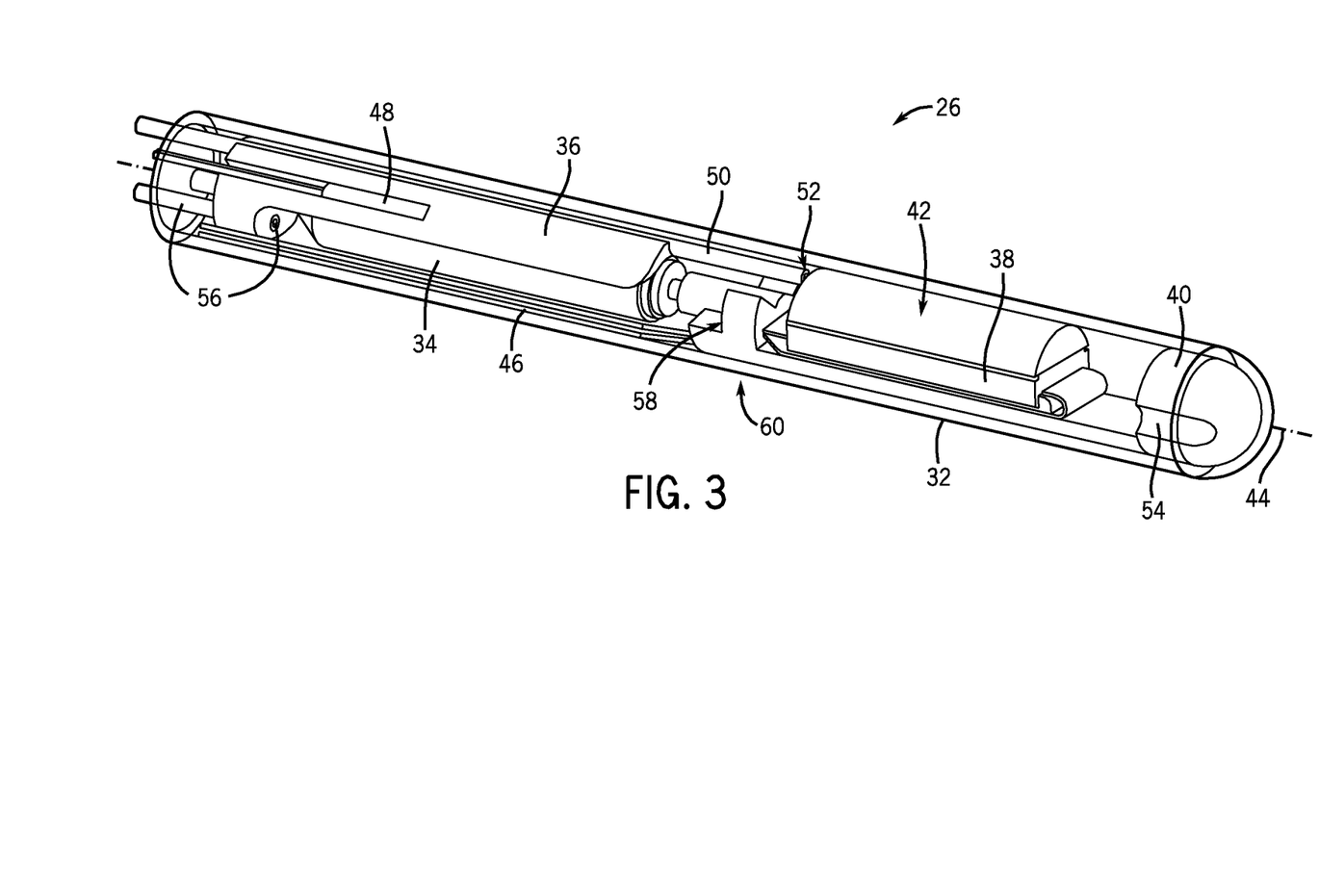
FIG. 3 is a perspective side view of an exemplary embodiment of an imaging catheter tip, in accordance with aspects of the present technique.

FIG. 3 depicts an exemplary embodiment of an imaging catheter tip 26. In the illustrated embodiment, the imaging catheter tip 26 includes a housing 32 which contains, among other things, a motor 34, a motor holder 36, a transducer 38, a transducer holder 40, and, optionally, a lens 42. Similar imaging catheter tips are described in U.S. Patent Application Publication Nos. 2007/0167813 filed on Jan. 18, 2007, 2007/0167821 filed on Nov. 30, 2005, 2007/0167824 filed on Jan. 11, 2006, 2007/0167825 filed on Jan. 11, 2006, and 2007/0167826 filed on Jan. 11, 2006, each to Warren Lee at al. as well as U.S. patent application Ser. No. 12/099,862 filed Apr. 9, 2008 to Warren Lee et al., each of which is incorporated herein by reference in its entirety for all purposes. The motor 34 may be used to oscillate the transducer 38 about an axis 44. The transducer 38 may, for example, be a 64-element phased array and may be oscillated about the axis 44 in order to generate real-time, three dimensional imaging by sweeping a two-dimensional slice over a three-dimensional volume.

In the illustrated embodiment, the motor holder 36 may serve several purposes with respect to the motor 34. First, the motor holder 36 may serve to fix the motor 34 in a specific position (e.g., centered relative to axis 44) within the tube. Second, the motor holder 36 may serve to support or constrain other components of the imaging catheter tip 26. One example of the components which may be supported by the motor holder 36 is a flexible interconnect cable 46 which may extend from the proximal end of the imaging catheter tip 26 and connect to the transducer 38. This flexible interconnect cable 46 may be used to send and receive electrical signals between the ultrasound imaging system 20 and the transducer 38 during imaging. In the illustrated embodiment, a thermistor 48 may be used to monitor the temperature of the motor 34 and motor holder 36.

Using the present technique, the imaging catheter tip 26 may be filled with acoustic coupling fluid at or near the time of use of the imaging catheter tip 26. For instance, the imaging catheter tip 26 may be filled during or immediately prior to an examination in which the imaging catheter tip 26 is used to collect imaging data. In the illustrated embodiment, a fill tube 50 may be used to deliver an acoustic coupling fluid into a distal portion of the imaging catheter tip 26 from the proximal end of the imaging catheter tip 26 at or near the time of use of the imaging catheter tip 26. If an acoustically suitable coupling fluid is used, it may be possible to exclude the lens 42 and use only the transducer 38 for imaging. Advantages of excluding the lens 42 may include a more simplified design, greater signal-to-noise ratio due to less lens attenuation, and less friction with which to load the motor 34.

The acoustic coupling fluid may be introduced by the fill tube 50 at the fill port 52. In the illustrated embodiment, the fill port 52 may be located near the proximal end of the transducer holder 40 though in other embodiments, the fill port 52 may be positioned at more distal or proximal locations relative to the transducer holder 40 than what is shown. In one embodiment, the distal portion of the imaging catheter tip 26 is filled while the distal end of the imaging catheter tip 26 is pointing downward. In such an embodiment, the acoustic coupling fluid may fill the distal portion of the imaging catheter tip 26 through capillary action between the transducer 38 (and lens 42, if used) and the housing 32 of the imaging catheter tip 26. The acoustic coupling fluid may fill the distal portion of the imaging catheter tip 26 until the entire portion is filled.

In some embodiments, the fill tube 50 may be a metal tube or other rigid tube. However, through the flexible shaft 28 of the imaging catheter 14, the fill tube 50 may be required to be somewhat flexible. Therefore, the fill tube 50 may be a combination of a rigid tube in the imaging catheter tip 26 coupled to a long, flexible tube through the flexible shaft 28. Within the flexible shaft 28, the fill tube 50 may be a discrete tube inserted into a larger lumen in the catheter. Alternatively, the fill tube 50 may be one, or possibly more, lumens integrated into the catheter construction. However, with either design, the fill tube 50 provides a leak-tight, pressure-capable connection to the imaging catheter tip 26 and the fill port 52.

As the acoustic coupling fluid is introduced into the distal portion of the imaging catheter tip 26 in the depicted embodiment, bubbles may develop in the acoustic coupling fluid. However, in the illustrated embodiment, a vent 54 may be used at the distal end of the transducer holder 40. This vent 54 may facilitate removal of the bubbles. It may also be possible for the operator of the imaging catheter tip 26 to use a simple "lasso" motion to force the bubbles to be removed through a vent tube 56 in response to centripetal forces. In other words, the vent 54 and vent tube 56 give the bubbles a route through which to exit the imaging catheter tip 26. The vent tube 56, which may receive expelled air and excess acoustic coupling fluid from the imaging catheter tip 26, may be similar to the fill tube 50 or may also be part of a lumen in the catheter. The vent tube 56 should also be leak-tight, but does not necessarily have to be able of sustaining high pressures, depending on the embodiment. In other embodiments, the expelled air and excess acoustic coupling fluid may simply pass around the other components in the imaging catheter tip 26, such as the signal cables and wiring.

Acoustic coupling fluids for use with the present technique may have one or more of the following properties: (1) sound velocity and density similar to water, (2) low tendency for releasing gas (in order to minimize bubbles from forming after filling), (3) biocompatibility, (4) the ability to wet the inner surfaces of the imaging catheter tip 26, and so forth. Several fluids have been tested and identified as possible candidates for the acoustic coupling fluid. These fluids include: (1) propylene glycol, (2) water, (3) ethanol, (4) polyethylene glycol, (5) 3M FC-3283 Fluorinert, and so forth. Other fluids may also prove suitable as this list is merely meant to be illustrative.

In one embodiment where propylene glycol is the acoustic coupling fluid, standard practices, such as flushing of the catheter prior to use, may have to be adjusted to accommodate the viscosity of the acoustic coupling fluid. For example, propylene glycol, compared to saline or water, may require higher pressures for a longer period of time in order to force the fluid through the fill tube 50 into the imaging catheter tip 26. In one embodiment, the procedure of filling the imaging catheter tip 26 using the present technique does not utilize separate equipment, such as pumping equipment, and does not require substantial operator involvement or actions.

Figure 4:
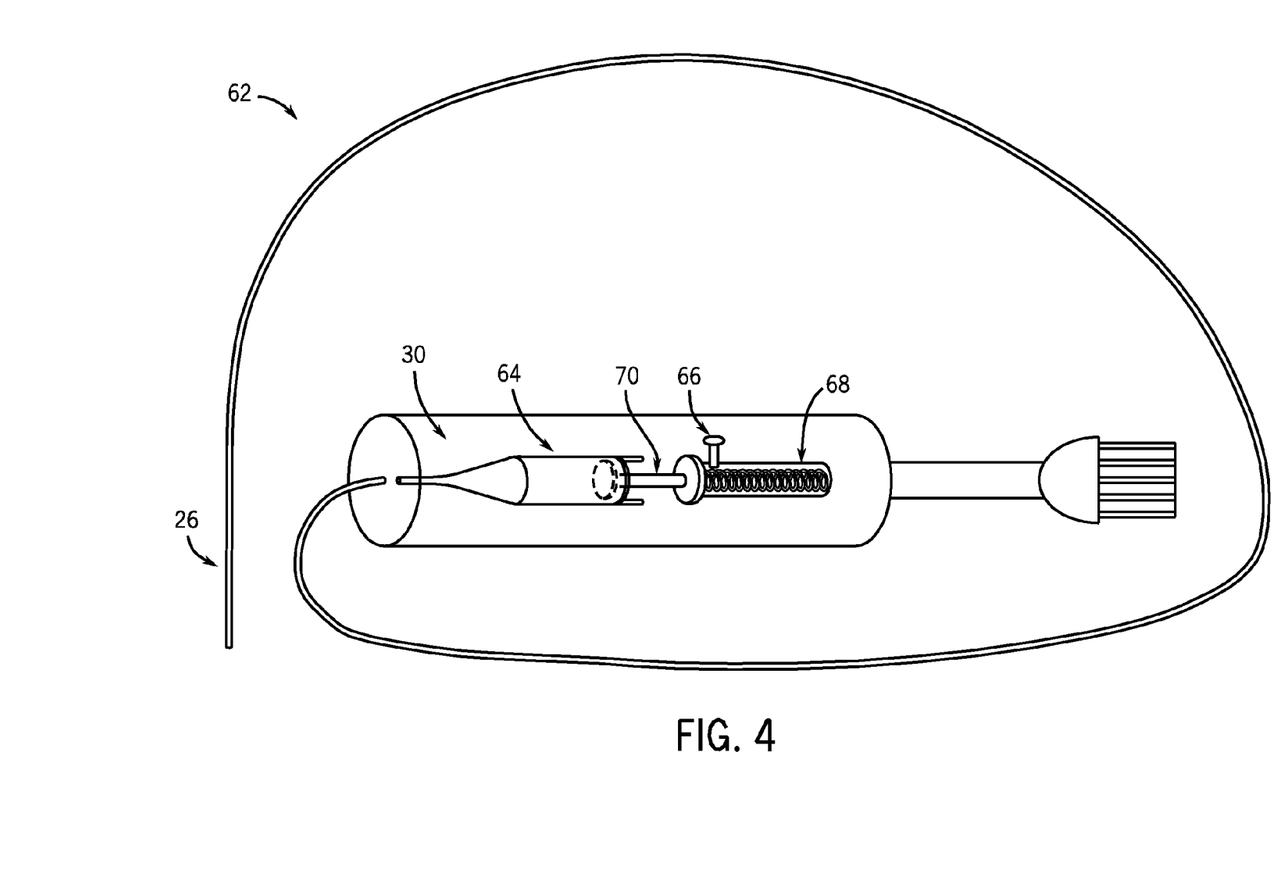
FIG. 4 is a perspective side view of an exemplary embodiment of an imaging catheter assembly, in accordance with aspects of the present technique.

FIG. 4 is a perspective side view of an exemplary embodiment of an imaging catheter assembly 62 for use with the present technique. In this embodiment, the imaging catheter 14 may be packaged with a fluid reservoir 64, such as a syringe, which has been preloaded with sterile acoustic coupling fluid. The fluid reservoir 64 may be a syringe, bag, bottle, or any other suitable fluid container. The fluid reservoir 64 may be sterilizable when loaded with the acoustic coupling fluid, easily coupled to the imaging catheter 14, and easily compressed to force the acoustic coupling fluid into the imaging catheter 14 via the fill tube 50. In some embodiments, the fluid reservoir 64 may be integrated into the imaging catheter handle 30 and thus invisible to the operator with the exception of a release mechanism 66, which may take the form of a button or latch on the imaging catheter handle 30.

In one embodiment, the operator may activate the release mechanism 66, releasing a biasing member 68 which may exert a known amount of force against a plunger 70 within the fluid reservoir 64. In turn, this may force the plunger 70 into the fluid reservoir 64 causing the acoustic coupling fluid to be delivered into the fill tube 50. The fill tube 50 may extend throughout the length of the flexible imaging catheter shaft 28. In the illustrated embodiment, the biasing member 68 is a spring configured to deliver a controlled force or controlled-rate displacement and may include a stop to limit the total displacement. In this manner, the total amount of acoustic coupling fluid introduced into the imaging catheter tip 26 may be limited.

By allowing the fluid reservoir 64 to fill the imaging catheter tip 26 with acoustic coupling fluid based on activation of the release mechanism 66, the fluid filling process may be simplified as well as ensuring that the correct amount of acoustic coupling fluid is delivered to the imaging catheter tip 26. As such, the fluid filling process may become more accurate and repeatable. In addition, using the present technique, the fluid filling process may be performed without requiring the operator to continually monitor the process because a pre-measured amount of acoustic coupling fluid may be placed in the fluid reservoir 64 and the mechanical characteristics of the release mechanism 66 and biasing member 68 may be determined to properly displace the acoustic coupling fluid. These specific mechanical characteristics of the release mechanism 66 and biasing member 68 may depend on numerous characteristics of the imaging catheter 14 and acoustic coupling fluid used, including the size of the fluid reservoir 64, the length and inside diameter of the fill tube 50, the interior volume of the imaging catheter tip 26, the viscosity of the acoustic coupling fluid, and so forth.

As noted above, the fluid reservoir 64, release mechanism 66, biasing member 68, and plunger 70 may be integrated within the imaging catheter handle 30. However, in some embodiments, these components may also be supplied separately from the imaging catheter 14. In this scenario, the acoustic coupling fluid may be delivered through a port at the proximal end of the imaging catheter 14 to which the fluid reservoir 64, such as a syringe, is coupled. In addition, the release mechanism 66, biasing member 68, and plunger 70 which force the acoustic coupling fluid from the fluid reservoir 64 may be integrated with the fluid reservoir 64 as a single disposable unit, or may be separate and reusable.

Figure 5:
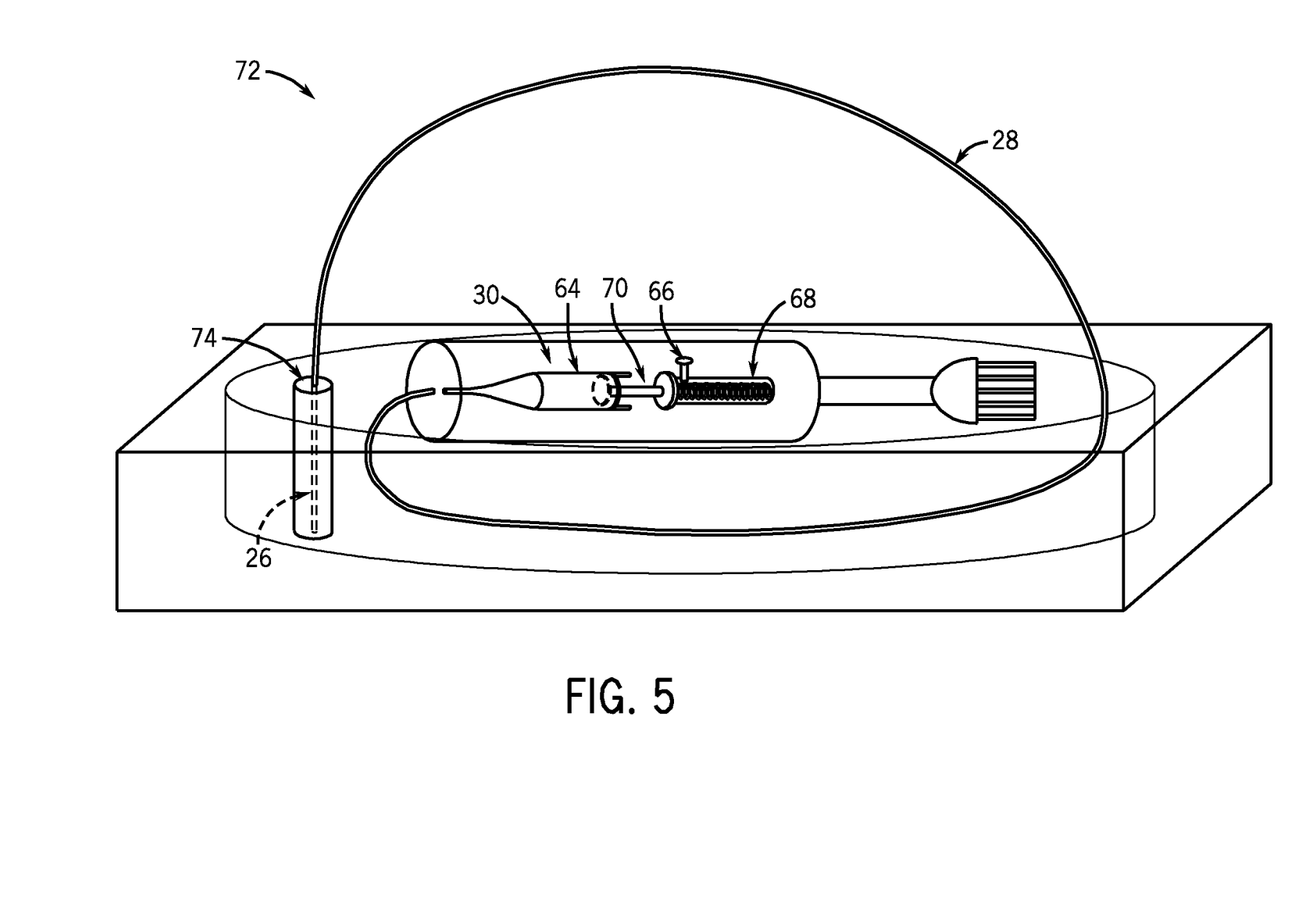
FIG. 5 is a perspective side view of an exemplary embodiment of imaging catheter packaging, in accordance with aspects of the present technique.

Referring now to FIG. 5, an embodiment is depicted in which the packaging 72 of the imaging catheter is designed to accommodate the automatic fill function. After testing the imaging catheter 14 using manufacturing and testing methods described in greater detail below, the imaging catheter 14 may be packaged with a fluid reservoir 64 which has been preloaded with sterile acoustic coupling fluid, at which point the imaging catheter packaging 72 may be shipped to an end user of the imaging catheter 14. As such, the preloading of the fluid reservoir 64 and the eventual filling of the imaging catheter tip 26 with the acoustic coupling fluid may occur at different locations and during different time periods. For instance, the preloading of the fluid reservoir 64 may occur at a manufacturing facility while the actual filling of the imaging catheter tip 26 may occur at a hospital during an examination where the imaging catheter 14 is used to collect ultrasound images from a patient. Therefore, the preloading of the fluid reservoir 64 may occur days, weeks, or even months before the imaging catheter tip 26 is actually filled.

In one such packaging implementation, the operator may remove the imaging catheter tip 26 from the packaging 72 and place it in a tip holder 74 within the packaging 72. For instance, the imaging catheter 14 may originally be coiled within the packaging 72. Then, upon opening the packaging 72, the operator may uncoil the imaging catheter 14 from the packaging 72 and place the imaging catheter tip 26 in the tip holder 74, which may be a cutout in the packaging 72 configured to hold the imaging catheter tip 26. The tip holder 74 may ensure that the distal end of the imaging catheter tip 26 points downward during the filling process. In some embodiments, in order to ensure that the imaging catheter tip 26 will only be filled when it is oriented downward, the release mechanism 66 may be positioned or may incorporate a mechanism which only allows the release mechanism 66 to be activated when properly oriented.

Figure 6:
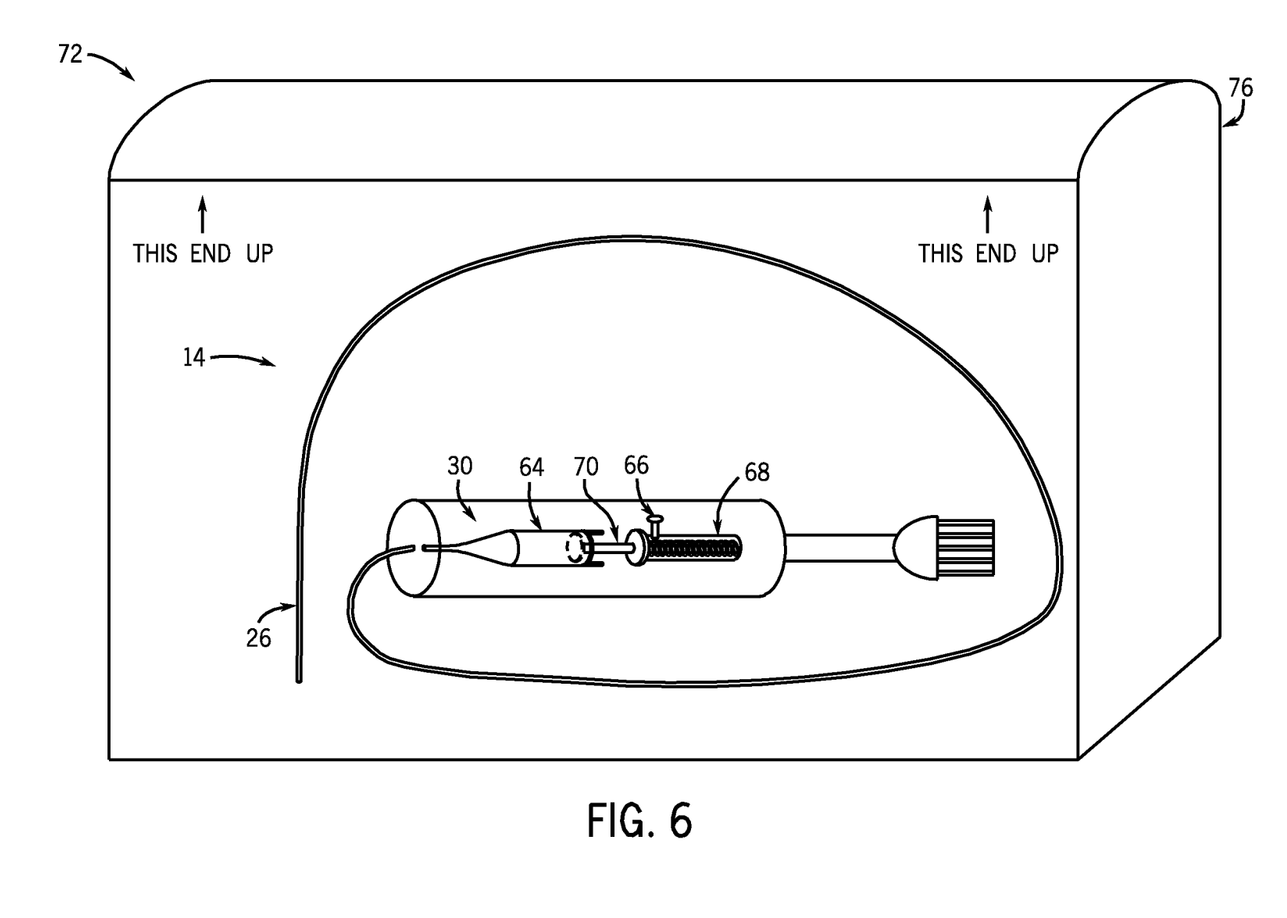
FIG. 6 is a perspective side view of another exemplary embodiment of imaging catheter packaging, in accordance with aspects of the present technique.

FIG. 6 is a perspective side view of another exemplary embodiment of imaging catheter packaging 72 using the present technique. In the illustrated embodiment, the entire imaging catheter 14, including the imaging catheter tip 26, shaft 28, and handle 30 may be packaged in a box 76 that is designed or labeled to be stood on one end so that the distal end of the imaging catheter tip 26 points downward within the box 76. For example, in one embodiment, the box 76 may have a "This End Up" label that may aid the operator in determining which direction to orient the box 76. In addition or alternatively, the box 76 may have rounded edges or sides that prevent the box 76 from being stood on an improper facing. Therefore, in orienting the box properly, the operator orients the imaging catheter tip 26 downward prior to fluid filling.

Prior to use, the operator may activate the release mechanism 66 which, in turn, releases the biasing member 68 such that acoustic coupling fluid is caused to move through the imaging catheter 14 into the imaging catheter tip 26. The release mechanism 66 may be activated while the imaging catheter 14 is still within the packaging 72. For instance, the release mechanism 66 may be activated through the packaging such that the operator may activate the release mechanism 66, and thereby cause the imaging catheter tip 26 to be filled with fluid, without removing the imaging catheter 14 from the packaging 72. Alternatively, the release mechanism 66 may be activated after opening the packaging 72 or a window in the packaging. In addition, as discussed above, the release mechanism 66 may incorporate a mechanism which only allows it to be activated when properly oriented.

Figure 7:
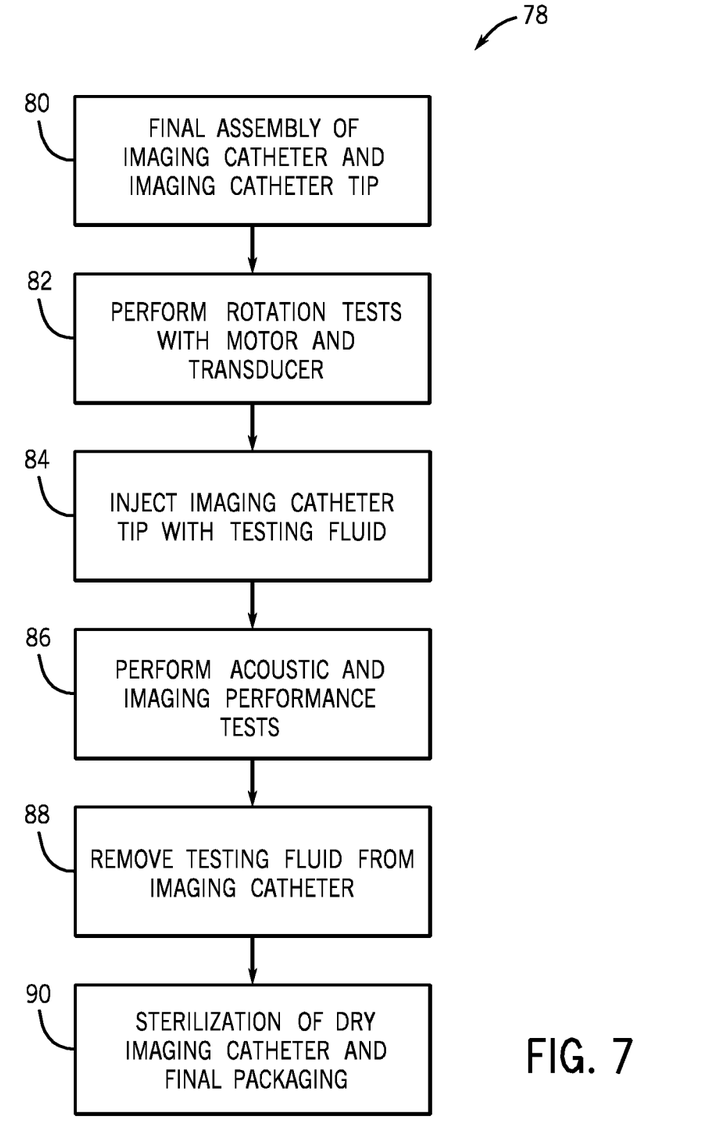
FIG. 7 is a process flow diagram of an exemplary method of manufacturing and testing the imaging catheter, in accordance with aspects of the present technique.

While the preceeding discussion relates to the packaging of an imaging catheter tip 26 which is fluid fillable, before packaging the imaging catheter 14 must be manufactured and tested. FIG. 7 is a process flow diagram of an exemplary method 78 of manufacturing and testing the imaging catheter 14. The method starts at step 80 with the final assembly of the imaging catheter 14 and associated imaging catheter tip 26. After final assembly 80, testing of the imaging catheter 14 may begin at step 82 where rotation of the motor 34 and transducer 38 is tested to make sure that the motor 34 is capable of oscillating the transducer 38 throughout an acceptable range of rotation.

Next, at step 84, the imaging catheter tip 26 may be injected with a testing fluid. The testing fluid may only be required for a short period of time and may be of low viscosity and high vapor pressure so that it can be evaporated after testing by placing the imaging catheter 14 at a high temperature and low pressure (i.e., an oven, a vacuum, or a vacuum oven). The testing fluid may be the same as or different from the acoustic coupling fluid which will be used in operation with the imaging catheter 14. In fact, in many instances, it may be useful to test with a different fluid since the acoustic coupling fluids that are normally used during use of the imaging catheter 14 may have higher viscosities and, thus, may be more difficult to remove prior to final packaging. For instance, it may be useful to use a relatively volatile, low-residue acoustic coupling fluid such as water or FC-3283 Fluorinert as the testing fluid. In some implementations, the testing fluid may be injected into the imaging catheter tip 26 before the rotation testing described above is performed.

At step 86, acoustic and imaging performance tests may be performed. In order to perform the acoustic and imaging tests, it may not be necessary to entirely fill the imaging catheter tip 26 with testing fluid. Rather, the imaging catheter tip 26 may be filled just enough to complete the testing. Doing so may reduce the possibility of leakage into the motor 34 during testing. In addition, the load on the motor 34 may be minimized and performance of the motor 34 preserved as much as possible for actual use.

Next, the testing fluid may be removed at step 88. The removal may be accomplished in various ways. For instance, the imagining catheter 14 may be placed in a vacuum oven to apply vacuum and heat between 35° C. and 80° C. (e.g., approximately 50° C.) in order to completely dry the imaging catheter 14. In addition, a dry inert gas, such as nitrogen, may be flushed through the catheter for a period of time to expedite removal of evaporated testing fluid and thereby keep the partial pressure of the testing fluid in the tip low and expedite evaporation and drying. Following removal of the testing fluid, the dried imaging catheter 14 may be sterilized and packaged for final shipment at step 90. The sterilization may, for instance, be accomplished using Ethylene Oxide (EtO) sterilization.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. An imaging catheter assembly, comprising:
   an imaging catheter comprising an imaging catheter tip; and
   an imaging catheter handle separate from the imaging catheter and coupled to the imaging catheter via a flexible shaft, wherein the imaging catheter handle comprises:
     a fluid reservoir connected to the imaging catheter and configured to deliver fluid through a proximal end of the imaging catheter tip, wherein the proximal end of the imaging catheter tip is an end of the imaging catheter tip that is closer to the imaging catheter handle than an opposite distal end;
     an actuatable release mechanism integrated into the imaging catheter handle and configured to cause delivery of the fluid to the imaging catheter tip when actuated with respect to the imaging catheter handle, wherein the actuatable release mechanism comprises a mechanism for preventing actuation of the actuatable release mechanism unless the imaging catheter tip is pointing downward;
     a plunger configured to displace fluid from the fluid reservoir; and
     a biasing member configured to exert a predetermined force against the plunger when the actuatable release mechanism is actuated with respect to the imaging catheter handle, thereby releasing the biasing member to bias against the plunger.

2. The imaging catheter assembly of claim 1, comprising a box configured to hold the imaging catheter, the imaging catheter handle, and the flexible shaft, wherein the box is adapted to hold the imaging catheter tip in a downward orientation when the actuatable release mechanism is actuated.

3. A packaging assembly, comprising:
   an imaging catheter comprising an imaging catheter tip and a fill mechanism; and
   a box configured to hold the imaging catheter tip in a fill orientation to facilitate filling the imaging catheter tip with acoustic coupling fluid upon activation of the fill mechanism, wherein the fill mechanism is configured to be activated only when the imaging catheter tip is held in the fill orientation.

4. The packaging assembly of claim 3, wherein the box comprises rounded edges which prevent the box from being placed in an orientation other than the fill orientation.

5. The packaging assembly of claim 3, wherein the box comprises at least one label indicating an orientation of the box which orients the imaging catheter tip in the fill orientation.

6. The packaging assembly of claim 3, wherein the fill mechanism is configured to be activated while the imaging catheter tip is held by the box.

7. The packaging assembly of claim 3, wherein the box comprises a receptacle region to hold the imaging catheter tip in the fill orientation.

8. The packaging assembly of claim 3, wherein the box holds the imaging catheter tip in the fill orientation without being attached to a device external to the box.

9. A packaging assembly, comprising:
- an imaging catheter comprising an imaging catheter tip and a fill mechanism; and
- a box configured to hold the imaging catheter tip in a fill orientation to facilitate filling the imaging catheter tip with acoustic coupling fluid upon activation of the fill mechanism, wherein the box comprises rounded edges which prevent the box from being placed in an orientation other than the fill orientation.

10. The packaging assembly of claim 9, wherein the box comprises at least one label indicating an orientation of the box which orients the imaging catheter tip in the fill orientation.

11. The packaging assembly of claim 9, wherein the fill mechanism is configured to be activated only when the imaging catheter tip is held in the fill orientation.

12. The packaging assembly of claim 9, wherein the fill mechanism is configured to be activated while the imaging catheter tip is held by the box.

13. The packaging assembly of claim 9, wherein the box comprises a receptacle region to hold the imaging catheter tip in the fill orientation.

14. The packaging assembly of claim 9, wherein the box holds the imaging catheter tip in the fill orientation without being attached to a device external to the box.

* * * * *